(12) United States Patent
Biesak et al.

(10) Patent No.: US 12,050,166 B2
(45) Date of Patent: Jul. 30, 2024

(54) TECHNIQUES FOR SENSING THE VISCOSITY OF CONCRETE IN A ROTATING CONTAINER

(71) Applicant: CIDRA CONCRETE SYSTEMS INC., Wallingford, CT (US)

(72) Inventors: John Biesak, Durham, CT (US); Douglas H. Loose, Southington, CT (US); James Michael Sullivan, East Hampton, CT (US); Paul Dolan, Portland, CT (US); Michael A. Davis, Glastonbury, CT (US); David Vincent Newton, Madison, CT (US); Charles Winston, Glastonbury, CT (US)

(73) Assignee: CIDRA CONCRETE SYSTEMS INC., Wallingford, CT (US)

( * ) Notice: Subject to any disclaimer, the term of this patent is extended or adjusted under 35 U.S.C. 154(b) by 0 days.

(21) Appl. No.: 17/682,183

(22) Filed: Feb. 28, 2022

(65) Prior Publication Data
US 2022/0178806 A1 Jun. 9, 2022

Related U.S. Application Data

(63) Continuation of application No. 16/638,258, filed as application No. PCT/US2018/047429 on Aug. 22, 2018, now Pat. No. 11,275,009.
(Continued)

(51) Int. Cl.
*G01N 11/14* (2006.01)
*G01F 22/00* (2006.01)
(Continued)

(52) U.S. Cl.
CPC ............ *G01N 11/14* (2013.01); *G01F 22/00* (2013.01); *G01N 33/383* (2013.01); *G01N 2011/0073* (2013.01)

(58) Field of Classification Search
CPC ... B01F 15/00246; B60P 3/16; G01N 33/383; G01N 2011/0046; G01N 11/00; G01N 11/10
See application file for complete search history.

(56) References Cited

U.S. PATENT DOCUMENTS 2,643,542 A 6/1953 Cronk
3,147,612 A 9/1964 Evans
(Continued)

OTHER PUBLICATIONS

Sofiane Amziane et al., "Feasibility of Using a Concrete Mixing Truck as a Rheometer", National Institute of Standards and Testing, NISTR 7333, Sep. 2006. (Year: 2006).*
(Continued)

*Primary Examiner* — Alexander A Mercado
(74) *Attorney, Agent, or Firm* — Ware, Fressola, Maguire & Barber LLP (57) ABSTRACT

A system for sensing the volume and/or viscosity of a slurry (e.g., like concrete) contained in a rotating container or drum, having a sensor and a signal processor. The sensor is configured to attach inside a rotating container or drum having a known geometry, sense angular positions of the sensor and also sense associated entry and exit points when the sensor enters and exits the slurry, including concrete, contained in the rotating container or drum, and provide signaling containing information about the angular positions and the associated entry and exit points. The signal processor receives the signaling, and determines corresponding signaling containing information about a volumetric amount, or a viscosity, or both, of the slurry in the rotating container or drum, based upon the signaling received.

18 Claims, 8 Drawing Sheets

The System

Related U.S. Application Data (60) Provisional application No. 62/548,683, filed on Aug. 22, 2017, provisional application No. 62/548,699, filed on Aug. 22, 2017.

(51) Int. Cl.
   *G01N 33/38* (2006.01)
   *G01N 11/00* (2006.01)

(56) References Cited

U.S. PATENT DOCUMENTS

| | | | |
|---|---|---|---|
| 3,237,437 A | 3/1966 | Hilkemeier | |
| 3,403,546 A | 10/1968 | Stratton | |
| 3,640,121 A | 2/1972 | Mercier | |
| 4,097,925 A * | 6/1978 | Butler, Jr. | B28C 5/4213 366/59 |
| 4,356,723 A | 11/1982 | Fay | |
| 4,578,989 A | 4/1986 | Scott | |
| 4,900,154 A | 2/1990 | Waitzinger | |
| 5,541,855 A | 7/1996 | Enzler | |
| D638,729 S | 5/2011 | Beaupre | |
| 8,764,272 B2 | 7/2014 | Hazrati | |
| 9,199,391 B2 | 12/2015 | Beaupre | |
| 9,429,559 B2 | 8/2016 | Radjy | |
| 9,518,870 B2 | 12/2016 | Verdino | |
| 9,789,629 B2 | 10/2017 | Koehler | |
| 9,833,928 B2 | 12/2017 | Bonilla Benegas | |
| 10,041,928 B2 | 8/2018 | Berman | |
| 10,126,288 B2 | 11/2018 | Radjy | |
| 10,156,547 B2 | 12/2018 | Biesak | |
| 10,183,418 B2 * | 1/2019 | Jordan | B28C 5/422 |
| 10,414,067 B2 * | 9/2019 | Datema | G06Q 10/06315 |
| 10,520,410 B2 | 12/2019 | Beaupre | |
| 10,739,328 B2 | 8/2020 | Baird | |
| 10,877,017 B2 | 12/2020 | Radjy | |
| 2009/0171595 A1 * | 7/2009 | Bonilla Benegas | B28C 5/422 702/41 |
| 2012/0204625 A1 * | 8/2012 | Beaupre | B28C 7/024 73/54.31 |
| 2014/0297204 A1 | 10/2014 | Biesak | |
| 2015/0082862 A1 * | 3/2015 | Loose | G01N 29/028 73/19.03 |
| 2015/0212061 A1 | 7/2015 | Radjy | |
| 2015/0355160 A1 * | 12/2015 | Berman | G01N 27/048 73/54.03 |
| 2016/0018383 A1 | 1/2016 | Radjy | |
| 2016/0223512 A1 | 8/2016 | Radjy | |
| 2017/0108421 A1 | 4/2017 | Beaupre et al. | |
| 2017/0212094 A1 | 7/2017 | Radjy | |
| 2017/0217047 A1 * | 8/2017 | Leon | B28C 5/4231 |
| 2017/0219553 A1 | 8/2017 | Radjy | |
| 2020/0217833 A1 | 7/2020 | Davis | |
| 2021/0031407 A1 | 2/2021 | Roberts | |
| 2021/0055195 A1 | 2/2021 | Beaupre | |

OTHER PUBLICATIONS

Ahmed Jarray et al., "Scaling of Wet Granular Flows in a Rotating Drum", The European Physical Journal Conferences, Jun. 2017. (Year: 2017).*

* cited by examiner

*FIG. 2:* Ready mix truck with arrow pointing to hatch door indicating potential location of AIRtrac™ sensor installation.

*FIG. 3:* Hatch door with AIRtrac™ sensor installed.

A system 10 for sensing the volume and/or viscosity of concrete, e.g., contained in a rotating container or drum:

Sensor 100 configured to attach inside a rotating container or drum having a known geometry, sense angular positions of the sensor and also sense associated entry and exit points when the sensor enters and exits a slurry (e.g. like concrete) contained in the rotating container or drum, and provide signaling $S_{in}$ containing information about the angular positions and the associated entry and exit points, e.g., having an acoustic transducer with an actuator and receiver, a 3-axis accelerometer, pressure sensors, etc.

Signal processor or processing module 12 configured at least to:

respond to the signaling $S_{in}$; and provide corresponding signaling $S_{out}$ containing information about a volumetric amount, or a viscosity, or both, of the slurry (e.g., concrete) in the rotating container or drum, based upon the signaling received.

Other signal processor circuits or components 14 that do not form part of the underlying invention, e.g., including input/output modules, one or more memory modules, data, address and control busing architecture, etc.

$S_{in}$ $S_{out}$

*FIG. 6:* The System

TECHNIQUES FOR SENSING THE VISCOSITY OF CONCRETE IN A ROTATING CONTAINER

CROSS-REFERENCE TO RELATED APPLICATIONS

This application is a continuation of, and claims benefit to, patent application Ser. No. 16/638,258, filed 11 Feb. 2020, which corresponds to PCT application no. PCT/US2018/047429, filed 22 Aug. 2018, which claims benefit to provisional patent application Ser. No. 62/548,683, filed 22 Aug. 2017, as well as provisional patent application Ser. No. 62/548,699, filed 22 Aug. 2017; which are all hereby incorporated by reference in their entirety.

This application is related to patent application Ser. No. 14/350,711, filed 9 Apr. 2014, which corresponds to PCT/US2012/060822, filed 18 Oct. 2012, claiming benefit to provisional patent application Ser. Nos. 61/548,549 and Ser. No. 61/548,563, both filed 18 Oct. 2011; which are all incorporated by reference in their entirety.

The aforementioned applications were all assigned to the assignee of the present application, which builds on this family of technology.

BACKGROUND OF THE INVENTION

1. Field of Invention

This invention relates to a technique for sensing the volume and/or viscosity of concrete in a rotating container or drum.

2. Description of Related Art

The assignee of the present invention has developed a means of measuring entrained air in wet concrete, which is disclosed in the aforementioned patent application Ser. No. 14/350,711. The measurement device or acoustic probe is called, or known in the industry as, AIRtrac™ or AIRtrac Mobile™. The AIRtrac™ sensor may be permanently installed on a rotating container/concrete mixer drum or on the hatch door of a concrete mixer drum.

Figure 1A:
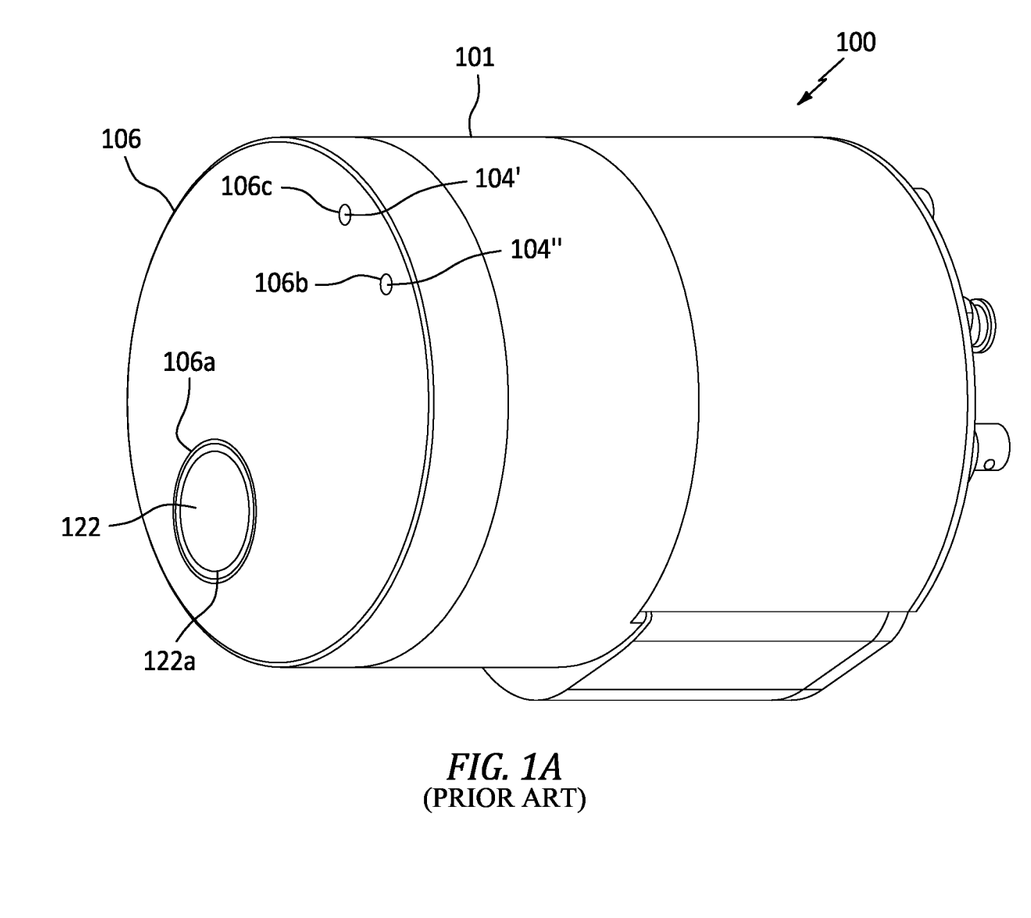
FIG. 1a is a perspective view of an acoustic probe that may be used in some embodiments of the present invention.
Figure 1B:
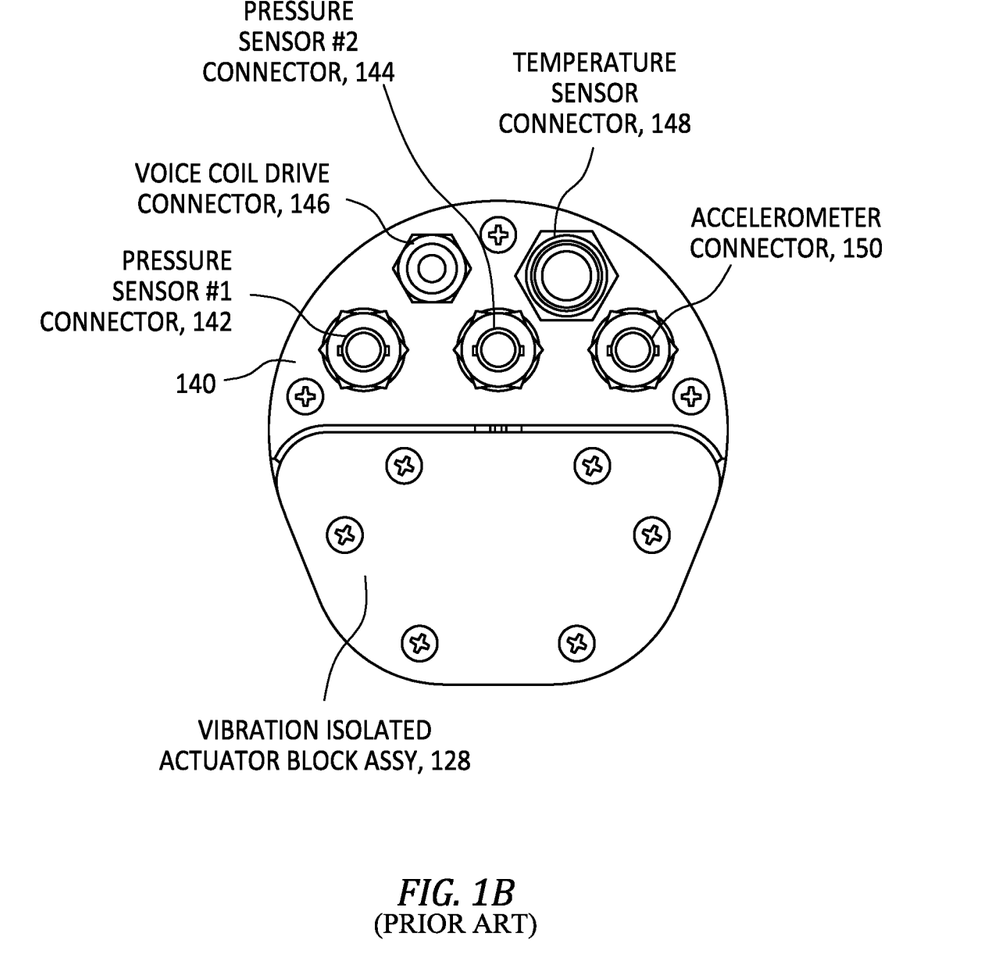
Figure 1C:
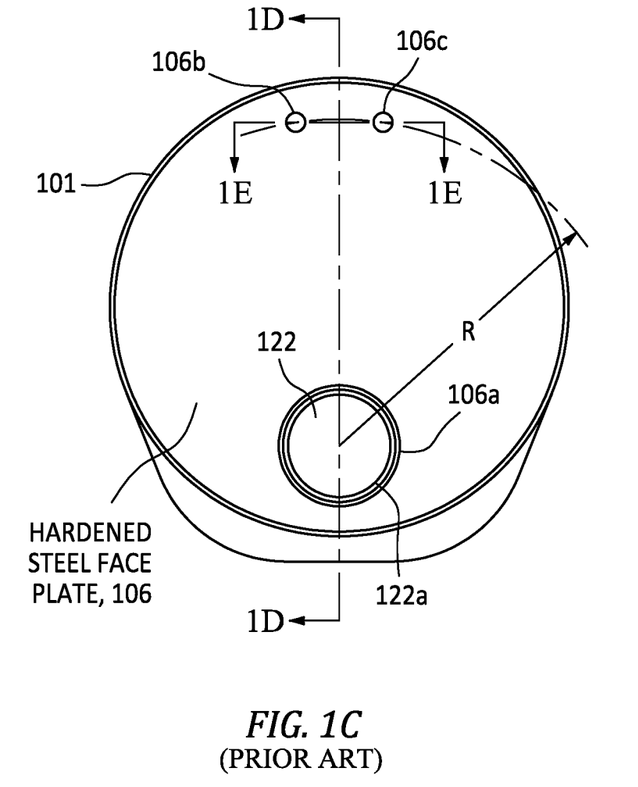

Consistent with that disclosed in the aforementioned patent application Ser. No. 14/350,711, and by way of example, FIGS. 1a to 1e show the AIRtrac™ sensor, that is generally indicated as 100 and may include an acoustic-based air probe like element 101. The acoustic-based air probe 101 may include an acoustic source generally indicated as 102 (see FIG. 1d) configured to provide an acoustic signal into a mixture of concrete; and an acoustic receiver generally indicated as 104 (see FIG. 1e) configured to be substantially co-planar with the acoustic source 102, to respond to the acoustic signal, and to provide signaling containing information about the acoustic signal injected into the mixture of concrete. By way of example, the acoustic source 102 may consist of an arrangement of parts and components and is best shown in detail in FIG. 1d. By way of example, the acoustic receiver 104 may consist of at least an arrangement of one or more transducers and fills and is best shown in FIG. 1e.

Figure 1D:
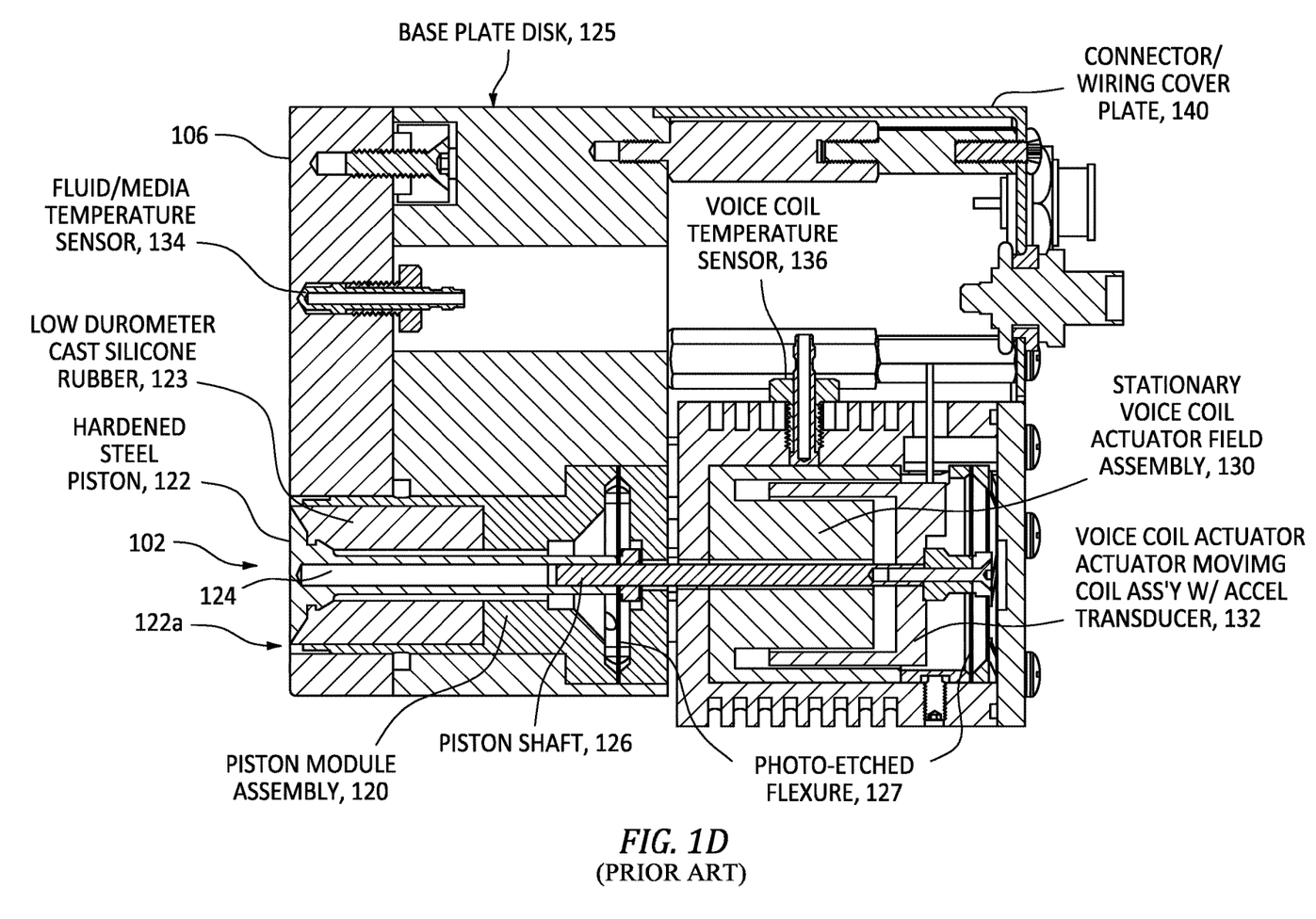
FIG. 1d is a sectional view of the end the acoustic probe shown in FIG. 1c along section lines A-A.
Figure 1E:
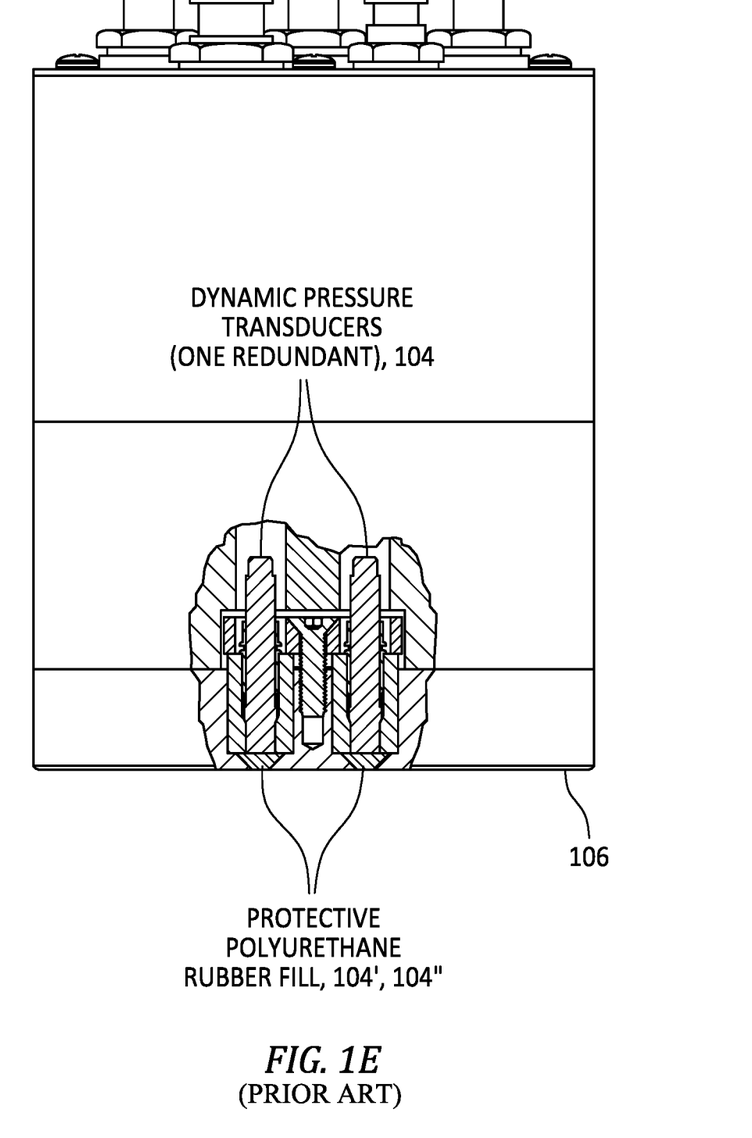
FIG. 1e is a sectional view of the end the acoustic probe shown in FIG. 1c along section lines B-B.

The acoustic-based air probe 101 may include a planar probing surface 106 having a first aperture 106a formed therein configured to receive part of the acoustic source 102, including a hardened steel piston 122, as best shown in FIG. 1d. At the interface with the planar probing surface 106, the hardened steel piston 122 is surrounded by a circumferential channel 122a, so as not to be in physical contact with the planar probing surface 106. The planar probing surface 106 may include at least one second aperture 106b, 106c formed therein configured to receive at least one part 104', 104" of the acoustic receiver 104. The part 104', 104" are shown as a protective polyurethane rubber member in FIG. 1e. The planar probing surface 106 may be configured as a hardened steel face plate, although the scope of the invention is intended to include using other type or kinds of materials either now known or later developed in the future. The acoustic receivers 104 are configured in relation to the center of the hardened steel piston 122 of the acoustic source 102 and defined by a radius R, as best shown in FIG. 1c, so that the acoustic receivers 104 are arranged and configured substantially on the circumference of a circle defined by the radius R from the center of the hardened steel piston 122.

The acoustic receiver 104 may include, or take the form of, a dynamic pressure transducer, as best shown in FIG. 1e.

In operation, and by way of example, the acoustic receiver 104 may be configured to receive acoustic signals, e.g., having a frequency in a range of about 100-500 Hz, including 330 Hz, although the scope of the invention is intended to include using other frequencies and other ranges either now known or later developed in the future.

By way of example, the acoustic source 102 may include, or take the form of, or be configured as, a floating mass, consistent with that shown in FIG. 1d.

In FIG. 1d, the acoustic source 102 is shown in the form of a piston module assembly 120 having the rigid hardened steel piston 122 configured with a channel 124 to receive, or be coupled to, a piston shaft 126. The acoustic-based air probe 101 has a base plate disk 125 that contains the piston module assembly 120, as well as other components in FIG. 1d. The rigid hardened steel piston 122 is enclosed, surrounded and configured to move in relation to a low durometer cast silicone rubber 123 and photo-etched flexures 127, so as to provide the floating mass aspect of the acoustic source 102. The low durometer cast silcone rubber 123 may also be configured to perform sealing functionality in relation to the mixture of the concrete. The acoustic source 102 may also include a vibration isolated actuator block assembly 128, best identified in FIG. 1b, having a stationary voice coil actuator field assembly 130 in combination with a voice coil actuator field assembly 132 having an accelerometer transducer configuration. The vibration isolated actuator block assembly 128 may be configured to drive and vibrate the piston shaft 126, consistent with that shown in FIG. 1d, so as to provide the acoustic signal to the mixture of the concrete when the acoustic-based air probe is inserted into the mixture. The apparatus 100 may also be configured with signal processing technology (not shown) for driving the acoustic source 102, as would be appreciated by a person skilled in the art.

The acoustic-based air probe 101 may include a fluid/media temperature sensor 134, consistent with that shown in FIG. 1d, configured to provide a temperature reading of the mixture.

The acoustic-based air probe 101 may include a voice coil temperature sensor 136, consistent with that shown in FIG. 1d, configured to provide a temperature reading of the stationary voice coil actuator field assembly 130.

The acoustic-based air probe 101 may include two acoustic receivers 104, 104', that may take the form of the two dynamic pressure transducers, consistent with that shown in FIG. 1e.

The acoustic-based air probe 101 may include some combination of a connector/wiring cover plate 140, and various connectors configured in relation to the same, including a pressure sensor no. 1 connector 142 for providing the signaling in relation to one pressure sensor, a pressure sensor no. 2 connector 144 for providing the signaling in relation to the other pressure sensor, a voice coil drive connector 146 for providing the signaling in relation to the voice coil drive 130 (FIG. 1d), a temperature sensor connector 148 for providing the signaling in relation to a temperature, and an accelerometer connector 150 for providing the signaling in relation to the voice coil actuator moving coil assembly 132 (FIG. 1d), all shown in FIG. 1b.

SUMMARY OF THE INVENTION

The present invention provides a new use of air measurement information provided by the AIRtrac™ sensor, e.g., including quality of signal and other diagnostics to discern when the probe is submerged in concrete and when it's not. That air measurement information coupled with sensor location information provided by the AIRtrac™ sensor, estimated slump, drum speed, drum size and dimensions can all be used to give an accurate estimate of how much concrete is currently in the container/mixer drum. This will particularly useful when part of a load is discharged and a specific amount of concrete (what should be left in the drum) is required for another job.

By way of example, the AIRtrac™ sensor may be mounted on hatch door or side wall of mixer drum. Its power source can be inductive, solar or battery.

In operation, the AIRtrac™ sensor will report air content in the wet concrete. Once the concrete is covering the AIRtrac™ sensor, the AIRtrac™ will also begin to report real-time air by volume information.

Particular Embodiments

In its broadest sense, the present invention provides a new and unique system for sensing the volume and/or viscosity of a slurry (e.g., like concrete) contained in a rotating container or drum, having a sensor and a signal processor.

The sensor may be configured to attach inside a rotating container or drum having a known geometry, sense angular positions of the sensor and also sense associated entry and exit points when the sensor enters and exits the slurry, including concrete, contained in the rotating container or drum, and provide signaling containing information about the angular positions and the associated entry and exit points.

The signal processor may be configured to receive the signaling, and determine corresponding signaling containing information about a volumetric amount, or a viscosity, or both, of the slurry in the rotating container or drum, based upon the signaling received.

The system may also include one or more of the following features:

The sensor may include a 3-axis accelerometer configured to respond to the angular positions of the sensor at given times, and provide angular position signaling containing information about the angular positions of the sensor at the given times.

The signal processor may be configured to determine the volumetric amount based upon static pressure readings contained in the signaling received that increase when the sensor enters the concrete and decrease when the sensor exits the concrete.

The sensor may include a pressure transducer configured to sense static pressure when the sensor enters and exits concrete contained in the rotating container or drum and provide static pressure signaling containing information about the static pressure sensed.

The signal processor may be configured to determine the associated entry and exits points of the sensor using a least squares curve fitting algorithm.

The signal processor may be configured to determine the volumetric amount based upon acoustic energy readings contained in the signaling received that increases when the sensor enters the concrete and decreases when the sensor exits the concrete.

The sensor may include a piston arranged in the rotating container or drum and configured to generate pulses; and a pressure transducer arranged in the rotating container or drum at a known distance from the piston and configured to sense the pulses generated and provide acoustic energy signaling containing information about the pulses sensed, including where the magnitude of acoustic energy sensed by the pressure transducer is low when the pulses are generated and sensed in air, and where the magnitude of acoustic energy sensed by the pressure transducer is high when the pulses are generated and sensed in the concrete.

The signal processor may be configured to determine the viscosity based upon the amount of "tilt" of the concrete in the rotating container or drum and the speed of rotation of the rotating container or drum.

The signal processor may be configured to determine the amount of "tilt" of the concrete in the rotating container or drum based upon the angular positions and the associated entry and exit points when the sensor enters and exits concrete contained in the rotating container or drum.

The signal processor may be configured to determine the rotation speed of the rotating container or drum based upon the angular positions of the sensor contained in the signaling received.

The signaling may contain information about constituents of the concrete, including the amount of water, sand, rock and respective densities, and the signal processor may be configured to determine the slump of the concrete, based upon the signaling received.

The sensor may be mounted on a hatch door of the rotating container or drum, as well as other parts of the rotating container or drum.

The sensor is an acoustic-based sensor.

The Signal Processing Functionality

The signal processor may be configured to receive signaling containing information about angular positions of a sensor attach inside a rotating container or drum having a known geometry, as well as associated entry and exit points when the sensor enters and exits a slurry (e.g., like concrete) contained in the rotating container or drum, and determine corresponding signaling containing information about a volumetric amount, or a viscosity, or both, of the slurry in the rotating container or drum, based upon the signaling received.

BRIEF DESCRIPTION OF THE DRAWING

The drawing includes FIGS. 1a-6, which are not necessarily drawn to scale, as follows:

FIG. 1b is an axial view of one end the acoustic probe shown in FIG. 1a.

FIG. 1c is an axial view of another end the acoustic probe shown in FIG. 1a.

FIG. 5 includes FIGS. 5A and 5B, where

DETAILED DESCRIPTION OF BEST MODE OF THE INVENTION

Summary of Basic Invention

The AlRtrac™ mobile sensor measures air content by actively creating acoustic waves and measuring the speed of the waves in the concrete media. This is accomplished by using a piston to "pulse" the concrete and measuring the amount of time it takes for the pulse to travel through the concrete and be detected by a pressure transducer that is known distance away from the piston, e.g., consistent with that set forth above. This works very well for the determination of the air content of the concrete mixture but these components can also be used to measure other aspects of the concrete. The present invention discloses two additional measurements that can be made.

Volume of Concrete

Figure 4:
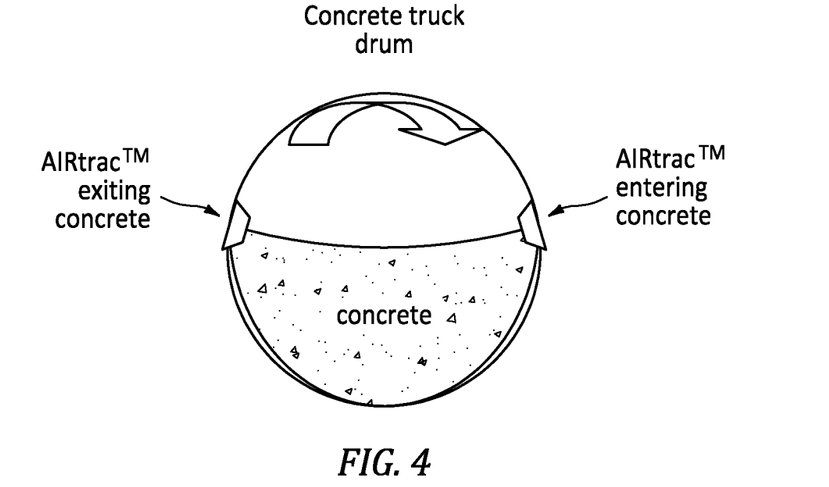
FIG. 4 is a diagram showing an end cross-section of a concrete truck drum having an AlRtrac™ sensor entering and exiting the concrete as the concrete truck drum.

One parameter that is often not known is the precise volumetric amount of concrete that is in a concrete truck, particularly after a partial pour has occurred. Some measurement techniques known in the art look at the hydraulic loading of the drum, however this is often inaccurate as it requires knowledge of the exact density of the concrete as well as the knowledge of other parameters such as the air content. Using the AlRtrac™ system a much more direct measurement can be made. This measurement technique utilizes the fact that the AlRtrac™ sensor is submerged under the concrete for part of the drums rotation and then is out of the concrete for the remainder. In addition, the AlRtrac™ device has a 3-axis accelerometer that is used to determine the angular position of the sensor at any given time. The combination of knowing the concrete entry and exit angles along with the geometry of the drum, the volume of the concrete can be calculated. FIG. 4 shows a diagram of how this can be achieved.

FIG. 4 shows an approximately half full drum. The AlRtrac™ sensor will enter the concrete at about +90 degrees from vertical and exit at about −90 degrees. This will give an indication that the concrete is occupying about ½ the drum and the volume can be calculated. A simple calculation can be made for other concrete entry/exit angles to yield volume.

The angle of the sensor is always available so the remaining aspect of the measurement is determination of the concrete entry and exit points. Two ways this can be accomplished utilize the pressure transducer. First, a static pressure can indicate when the sensor is under concrete. While in air above the concrete the pressure transducer will show close to 0 pressure, but as the senor enters the concrete the weight of the concrete will cause a pressure reading. This reading will increase until the sensor is at the bottom of the drum and then decrease until the sensor emerges from the concrete on the other side. Various analysis techniques including least squares curve fitting can be used to extrapolate the exact entry and exit points of the pressure sensor. A second detection technique can utilize the magnitude of the acoustic signal the pressure sensor sees as it is generated by the piston. Air is highly attenuative to acoustic waves so when the AlRtrac™ is in air the pressure transducer will see very little of the acoustic energy generated by the piston, while once the sensor is in the concrete the signal level will rise dramatically. This can also be used to determine when the AlRtrac™ sensor enters and leaves the concrete within the drum.

Viscosity of Concrete

Figure 5A:
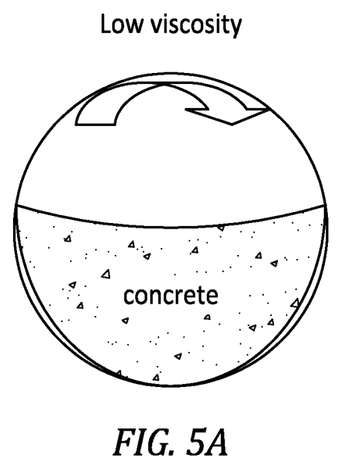
FIG. 5A is a diagram showing an end cross-section of a concrete truck drum with concrete having a low viscosity; and where
Figure 5B:
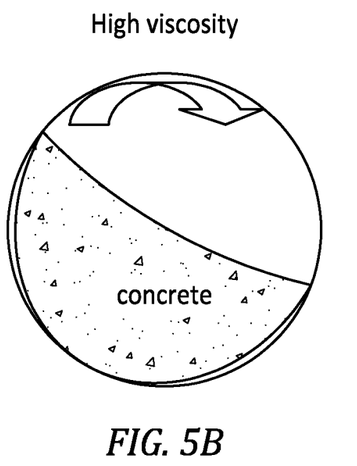
FIG. 5B is a diagram showing the end cross-section of the concrete truck drum with concrete having a high viscosity.

A second parameter of the concrete that the AlRtrac™ can determine is the viscosity of the concrete. The viscosity of a fluid is directly related to the ability of the fluid to flow. Therefore, in a rotating container or drum like a concrete truck a low viscosity fluid will remain very level while a very viscous fluid will tend to not flow very well and will ride up the wall of the drum as the drum exits the fluid. FIG. 5 shows diagrams of the effect.

The amount of the "tilt" of the concrete in the drum will depend on the viscosity of the fluid (or concrete) and the speed of rotation of the drum. The drum rotation speed can be determined by the 3-axis accelerometer and the "tilt" can be determined by the same techniques described above. With knowledge of these parameters along with geometric shape of the drum the concrete viscosity can be determined. Furthermore, with knowledge of the concrete constituents including amount of water, sand, rock and their respective densities, the slump of the concrete can be determined.

The System 10

Figure 6:
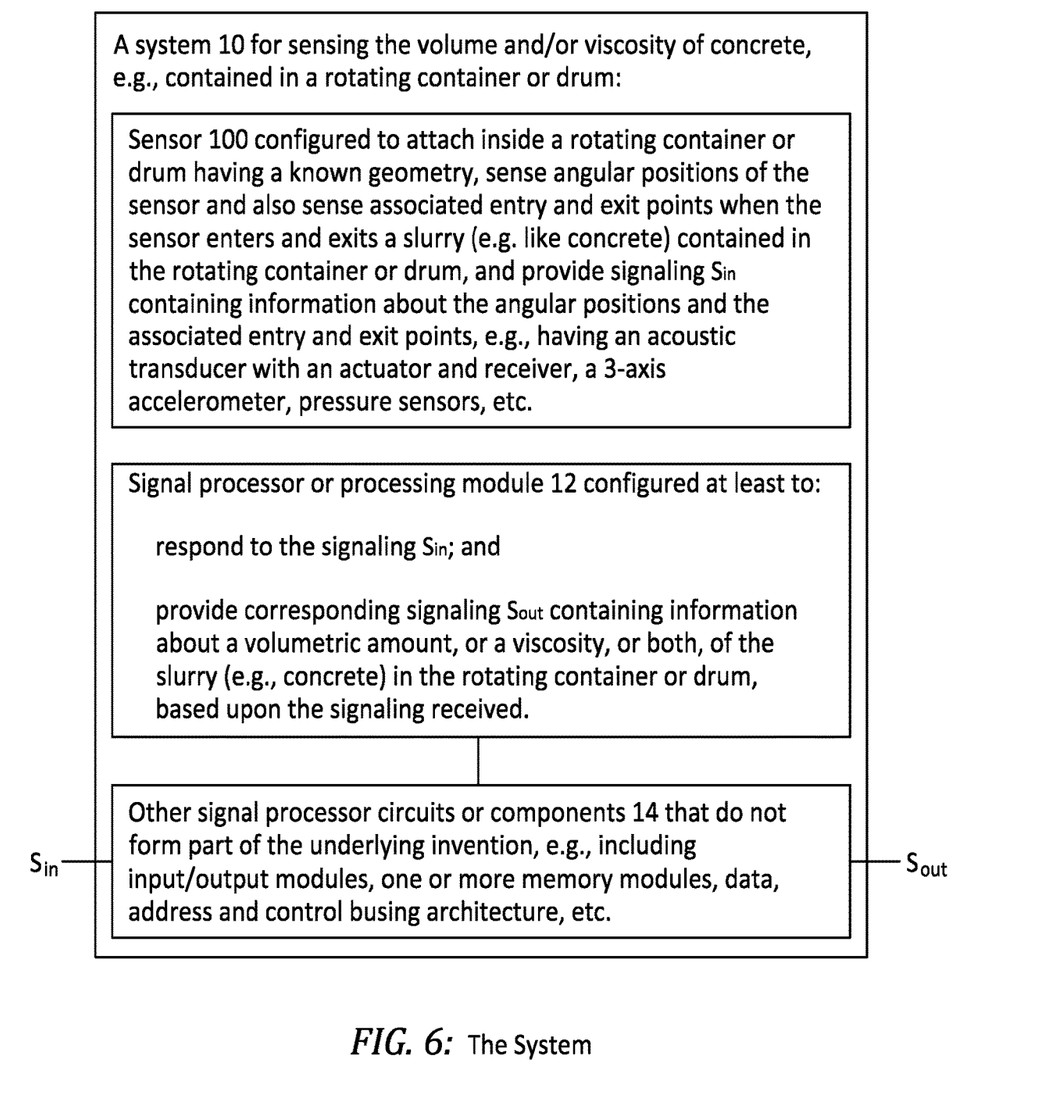
FIG. 6 is a block diagram of a system having a sensor and a signal processor or signal processing module for implementing the present invention.

FIG. 6 shows a system 10 having a sensor (e.g., such as an acoustic-based sensor like element 100) and a signal processor or signal processing module 12 for implementing the present invention.

Figure 2:
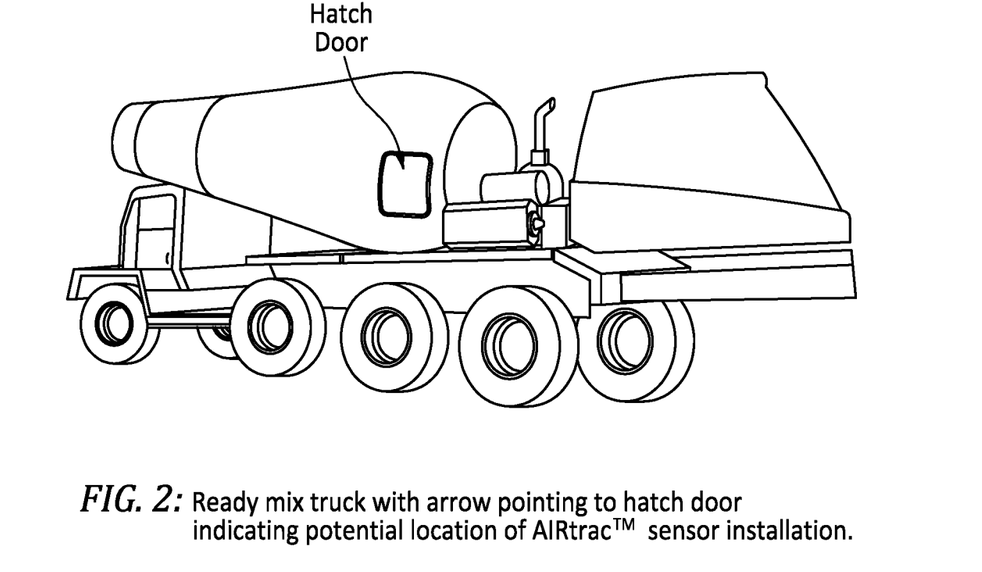
FIG. 2 is a photograph of a ready mix truck with arrow pointing to hatch door indicating potential location of AlRtrac™ sensor installation, which is provided as an example of an AlRtrac™ system installed on a hatch door, and where the hatch door may be located on mixer drum.
Figure 3:
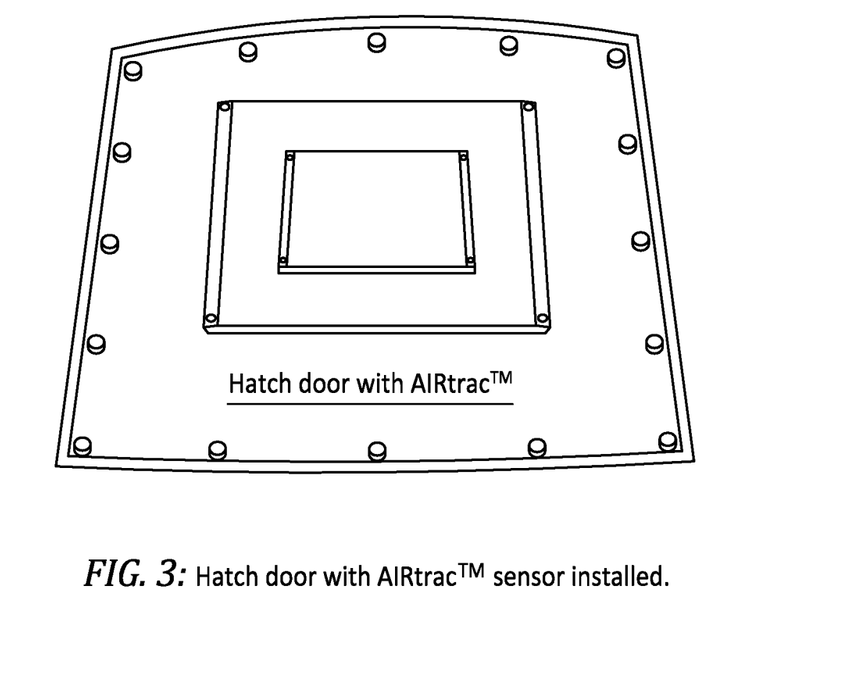
FIG. 3 is a photograph of a hatch door with AlRtrac™ sensor installed.

In operation, the sensor 100 may be configured to attach inside a rotating container or drum like that shown in FIGS. 2-3 having a known geometry, sense angular positions of the sensor as the drum rotates, and also sense associated entry and exit points when the sensor enters and exits a slurry (e.g., like concrete) contained in the rotating container or drum, and provide signaling containing information about the angular positions and the associated entry and exit points.

The signal processor 12 may be configured to receive the signaling sensed, and determine corresponding signaling containing information about a volumetric amount, or a viscosity, or both, of the slurry (like concrete) concrete in the rotating container or drum, based upon the signaling received.

The functionality of the signal processor or processor control module 12 may be implemented using hardware, software, firmware, or a combination thereof. In a typical software implementation, the processor module may include one or more microprocessor-based architectures having a microprocessor, a random access memory (RAM), a read only memory (ROM), input/output devices and control, data and address buses connecting the same, e.g., consistent with that shown in FIG. 6, e.g., see element 14. By way of example, the input/output devices may be configured to receive the signaling $S_{in}$ sensed by the sensor 100, and provide the signaling $S_{in}$ to the signal processor 12 for further processing. By way of further example, the input/output devices may be configured to receive the corresponding signaling $S_{out}$ from the signal processor 12, and provide the corresponding signaling $S_{out}$.

A person skilled in the art would be able to program such a microprocessor-based architecture(s) to perform and implement such signal processing functionality described herein without undue experimentation. The scope of the invention is not intended to be limited to any particular implementation using any such microprocessor-based architecture or technology either now known or later developed in the future.

The Acoustic-Based Sensor

By way of example, the present invention is disclosed based upon using the assignee's AIRtrac™ sensor. However, the scope of the invention is not intended to be limited to the same. For example, embodiments are envisioned, and the scope of the invention is intended to include, e.g. using other types or kinds of acoustic-based sensors either now known or later developed in the future that may be configured to attach inside a rotating container or drum having a known geometry, sense angular positions of the sensor and sense associated entry and exit points when the sensor enters and exits concrete contained in the rotating container or drum, and provide signaling containing information about the angular positions and the associated entry and exit points.

The Rotating Container or Drum

By way of example, the present invention is disclosed based upon using a rotating drum forming part of a concrete mixing truck. However, the scope of the invention is not intended to be limited to the same. For example, embodiments are envisioned, and the scope of the invention is intended to include, e.g. using other types or kinds of rotating containers or drums either now known or later developed in the future that may be configured to receive and contain concrete, as well as rotate and mix the concrete.

The Slurry (e.g., Concrete)

By way of example, the present invention is disclosed based upon mixing a slurry like concrete using a rotating drum. However, the scope of the invention is not intended to be limited to the same. For example, embodiments are envisioned, and the scope of the invention is intended to include, e.g. processing other types or kinds of slurries either now known or later developed in the future, including other types or kinds of slurries that are sensitive to the amount of entrained air contained therein, other types or kinds of or slurries that are mixed and poured from a rotating container or drum.

Means for Attaching

Means for attaching a sensor inside a rotating container or drum is known in the art, and the scope of the invention is not intended to be limited to any particular types or kinds thereof either now known or later developed in the future. By way of example, the sensor may include a sensor housing that may be fastened inside the rotating container or drum using fasteners like screws.

The Scope of the Invention

While the invention has been described with reference to an exemplary embodiment, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A system for sensing a viscosity of concrete in a rotating container or drum, comprising:
   a sensor having a 3-axis accelerometer and a pressure transducer, being configured to attach inside a rotating container or drum having a known geometry, sense angular positions of the sensor and sense associated entry and exit points when the sensor enters and exits concrete contained in the rotating container or drum, and provide signaling containing information about the angular positions and the associated entry and exit points; and
   a signal processor configured to
      receive the signaling,
      determine an amount of "tilt" of the concrete in the rotating container or drum based upon the angular positions and the associated entry and exit points when the sensor enters and exits concrete contained in the rotating container or drum;
      determine the speed of the rotating container or drum based upon the angular positions of the sensor;
      receive further signaling containing information about the known geometry; and
      determine corresponding signaling containing information about a viscosity of the concrete in the rotating container or drum, based upon the amount of "tilt" of the concrete in the rotating container or drum and the speed of the rotating container or drum determined in relation to the signaling received and the known geometry contained in the further signaling received.

2. A system according to claim 1, wherein the sensor comprises an acoustic probe having the 3-axis accelerometer configured to respond to the angular positions of the sensor at given times, and provide angular position signaling containing information about the angular positions of the sensor at the given times.

3. A system according to claim 2, wherein the acoustic probe includes the pressure transducer configured to sense static pressure when the sensor enters and exits concrete contained in the rotating container or drum and provide static pressure signaling containing information about the static pressure sensed.

4. A system according to claim 3, wherein the acoustic probe is mounted on a hatch door of the rotating container or drum.

5. A system according to claim 1, wherein the signal processor is configured to determine the associated entry and exits points of the sensor using a least squares curve fitting algorithm.

6. A system according to claim 1, wherein the sensor comprises an acoustic probe having
a piston arranged in the rotating container or drum and configured to generate pulses; and
the pressure transducer is arranged in the rotating container or drum at a known distance from the piston and configured to sense the pulses generated and provide acoustic energy signaling containing information about the pulses sensed, including where the magnitude of acoustic energy sensed by the pressure transducer is low when the pulses are generated and sensed in air, and where the magnitude of acoustic energy sensed by the pressure transducer is high when the pulses are generated and sensed in the concrete.

7. A system according to claim 1, wherein the signal processor is configured to determine the rotation speed of the rotating container or drum based upon the angular positions of the sensor contained in the signaling received.

8. A system according to claim 1, wherein the signaling contains information about constituents of the concrete, including the amount of water, sand, rock and respective densities, and the signal processor is configured to determine the slump of the concrete, based upon the signaling received.

9. A system according to claim 1, wherein the acoustic probe is an acoustic-based air probe.

10. A system comprising:
a signal processor configured to
receive signaling containing information about angular positions of a sensor having a 3-axis accelerometer and a pressure transducer attached inside a rotating container or drum having a known geometry, as well as associated entry and exit points when the sensor enters and exits a slurry, including concrete, contained in the rotating container or drum,
determine an amount of "tilt" of the concrete in the rotating container or drum based upon the angular positions and the associated entry and exit points when the sensor enters and exits concrete contained in the rotating container or drum;
determine the speed of the rotating container or drum based upon the angular positions of the sensor;
receive further signaling containing information about the known geometry; and
determine corresponding signaling containing information about a viscosity of the slurry in the rotating container or drum, based upon the amount of "tilt" of the concrete in the rotating container or drum and the speed of the rotating container or drum determined in relation to the signaling received and the known geometry contained in the further signaling received.

11. A system according to claim 10, wherein the system comprises an acoustic probe having the 3-axis accelerometer configured to respond to the angular positions of the sensor at given times, and provide angular position signaling containing information about the angular positions of the sensor at the given times.

12. A system according to claim 11, wherein the acoustic probe includes the pressure transducer configured to sense static pressure when the sensor enters and exits concrete contained in the rotating container or drum and provide static pressure signaling containing information about the static pressure sensed.

13. A system according to claim 10, wherein the sensor comprises an acoustic probe having
a piston arranged in the rotating container or drum and configured to generate pulses; and
the pressure transducer arranged in the rotating container or drum at a known distance from the piston and configured to sense the pulses generated and provide acoustic energy signaling containing information about the pulses sensed, including where the magnitude of acoustic energy sensed by the pressure transducer is low when the pulses are generated and sensed in air, and where the magnitude of acoustic energy sensed by the pressure transducer is high when the pulses are generated and sensed in the concrete.

14. A system according to claim 10, wherein the signal processor is configured to determine the associated entry and exits points of the sensor using a least squares curve fitting algorithm.

15. A system according to claim 10, wherein the signal processor is configured to determine the rotation speed of the rotating container or drum based upon the angular positions of the sensor contained in the signaling received.

16. A system according to claim 10, wherein the signaling contains information about constituents of the concrete, including the amount of water, sand, rock and respective densities, and the signal processor is configured to determine the slump of the concrete, based upon the signaling received.

17. A system for sensing a relative viscosity of concrete in a rotating container or drum, comprising:
a sensor having a 3-axis accelerometer and a pressure transducer, being configured to attach inside a rotating container or drum having a known geometry, sense angular positions of the sensor and sense associated entry and exit points when the sensor enters and exits concrete contained in the rotating container or drum, and provide signaling containing information about the angular positions and the associated entry and exit points; and
a signal processor configured to
receive the signaling,
determine an amount of "tilt" of the concrete in the rotating container or drum based upon the angular positions and the associated entry and exit points when the sensor enters and exits concrete contained in the rotating container or drum;
determine the speed of the rotating container or drum based upon the angular positions of the sensor;
receive further signaling containing information about the known geometry; and
determine corresponding signaling containing information about a relative viscosity of the concrete in the rotating container or drum, based upon the amount of "tilt" of the concrete in the rotating container or drum and the speed of the rotating container or drum determined in relation to the signaling received and the known geometry contained in the further signaling received.

18. A system according to claim 17, wherein
the sensor comprises an acoustic probe having the 3-axis accelerometer configured to respond to the angular positions of the sensor at given times, and provide angular position signaling containing information about the angular positions of the sensor at the given times;

the acoustic probe includes the pressure transducer configured to sense static pressure when the sensor enters and exits concrete contained in the rotating container or drum and provide static pressure signaling containing information about the static pressure sensed; and the signal processor is configured to receive the angular position signaling and the static pressure signaling and determine the relative viscosity based upon the angular position signaling and the static pressure signaling received.

\* \* \* \* \*